United States Patent
Chang et al.

[11] Patent Number: 5,874,309
[45] Date of Patent: *Feb. 23, 1999

[54] METHOD FOR MONITORING METAL CORROSION ON INTEGRATED CIRCUIT WAFERS

[75] Inventors: Chao-Hsin Chang; Hsien-Wen Chang; Chih-Chien Hung; Kuang-Hui Chang, all of Hsin-chu, Taiwan

[73] Assignee: Taiwan Semiconductor Manufacturing Company, Ltd., Hsin-Chu, Taiwan

[*] Notice: This patent issued on a continued prosecution application filed under 37 CFR 1.53(d), and is subject to the twenty year patent term provisions of 35 U.S.C. 154(a)(2).

[21] Appl. No.: 730,383
[22] Filed: Oct. 16, 1996
[51] Int. Cl.[6] .................................................. G01N 31/00
[52] U.S. Cl. ........................................ 436/6; 436/1; 436/5
[58] Field of Search .......................................... 436/6, 1, 5

[56] References Cited

U.S. PATENT DOCUMENTS

| | | |
|---|---|---|
| 4,800,165 | 1/1989 | Oka et al. ..................................... 436/6 |
| 5,075,235 | 12/1991 | Fuchs et al. .................................. 436/6 |
| 5,159,752 | 11/1992 | Mahant-Shetti et al. ................. 29/846 |
| 5,389,216 | 2/1995 | Balkanli .............................. 204/153.11 |
| 5,411,890 | 5/1995 | Falat ........................................... 436/6 |
| 5,481,198 | 1/1996 | Patel ......................................... 324/700 |

*Primary Examiner*—Lyle A. Alexander
*Attorney, Agent, or Firm*—George O. Saile; Stephen B. Ackerman; Larry J. Prescott

[57] ABSTRACT

A method and metal test pattern for monitoring metal corrosion susceptibility for integrated circuit wafers. Test patterns having an array of metal circles to simulate contact regions, an array of metal strips to simulate electrode regions, and a blanket metal layer to simulate bulk metal regions are formed. A first number of defects per unit area for the test patterns is measured, using a defect scan system. The test pattern wafers are then subjected to environmental stress conditions for a first time and a second number of defects per unit area for the test patterns is measured, again using a defect scan system. The difference between the second number and the first number is compared with a critical number. If excessive corrosion occurs the process for producing wafers is corrected before continuing to process product wafers.

10 Claims, 3 Drawing Sheets

METHOD FOR MONITORING METAL CORROSION ON INTEGRATED CIRCUIT WAFERS

BACKGROUND OF THE INVENTION

(1) Field of the Invention

This invention relates to the use of wafers having metal test patterns to monitor the metal corrosion susceptibility of integrated circuit wafers. More particularly this invention relates to a comparison of numbers of defects per unit area of test pattern wafers, which are processed with product wafers, before and after the test pattern wafers are subjected to a stress environment.

(2) Description of the Related Art

U.S. Pat. No. 5,411,890 to Falat describes using a tapered metal strip on a transparent substrate to monitor corrosion. Corrosion causes the boundary between reflective and non reflective regions to move across the substrate. This test site is quite different than that described in this invention.

U.S. Pat. No. 5,389,216 to Balkanli describes a method of detecting corrosion in underground pipes. The method uses an analysis of the response to injected current pulses to evaluate corrosion.

U.S. Pat. No. 5,481,198 to Patel measures the resistance of a buried neutral wire of underground electrical cables by injecting additional current into the wire and measuring the voltage drop across a known length. This measured resistance is used to determine the amount of corrosion of the underground cable.

U.S. Pat. No. 5,159,752 to Mahant-Shetti et al. uses a grid pattern of electrodes deposited on a semiconductor wafer to monitor corrosion. An electron beam is directed on the structure and a scanning electron microscope is used to observe emitted secondary electrons. The observed secondary electrons gives a picture related to the condition of the pattern, such as shorts, opens, etc. A stress environment is not used to accelerate corrosion.

The invention of this Patent Application uses a number of test patterns to simulate contact regions, electrode regions, and bulk metal regions. A stress environment is used to accelerate corrosion. The numbers of defects per unit area are measured before and after the test pattern wafers are subjected to the stress environment. A comparison of the numbers of defects per unit area before and after the test pattern wafers are subjected to the stress environment is used to monitor metal corrosion susceptibility of production wafers.

SUMMARY OF THE INVENTION

In the manufacture of integrated circuit wafers corrosion of metal elements, such as metal electrodes, metal contacts, or other metal features, can cause serious problems. Often this metal corrosion is the result of parts of the manufacturing process which have gone out of control thereby exposing the metals to an excess of chloride ions or the like. These conditions can affect a large number of product wafers before the corrosion becomes noticeable thereby compounding the problem of finding and correcting the process problem with the necessity of discarding a large number of product wafers.

It is an objective of this invention to provide a method of determining if a corrosion problem is present at the point of the process where corrosion problems are introduced thereby simplifying the problem of correcting the process problem and avoiding the necessity of discarding product wafers.

It is a further objective of this invention to provide a test device for use in determining if a corrosion problem is present at the point of the process where corrosion problems are introduced thereby simplifying the problem of correcting the process problem and avoiding the necessity of discarding product wafers.

This objectives are achieved by using specially designed test patterns on test wafers which can detect different types of corrosion, such as metal electrode sidewall corrosion, metal contact corrosion, or the like. These test wafers are processed with product wafers until the appropriate process point. The test patterns are then analyzed using a means for determining the number of defects per unit area for the test pattern and a first number of defects per unit area is stored. The test wafers are then exposed to environmental stress conditions, such as elevated temperature and relative humidity, for a period of time.

The test patterns are then analyzed a second time and a second number of defects per unit area is determined. Then the difference between the second number of defects per unit area and the first number of defects per unit area is compared with an allowable number of defects per unit area. If the difference between the second number of defects per unit area and the first number of defects per unit area is less than the allowable number of defects per unit area processing of the product wafers continues. If the difference between the second number of defects per unit area and the first number of defects per unit area is equal to or greater than the allowable number of defects per unit area processing of the product wafers is stopped until the process problems are corrected and continued production of defective wafers is avoided. Due to the design of the test patterns an analysis of the type of corrosion can be used to help determine the problems causing metal corrosion and the point in the process where the problems are occurring.

DESCRIPTION OF THE PREFERRED EMBODIMENTS

Figure 1:
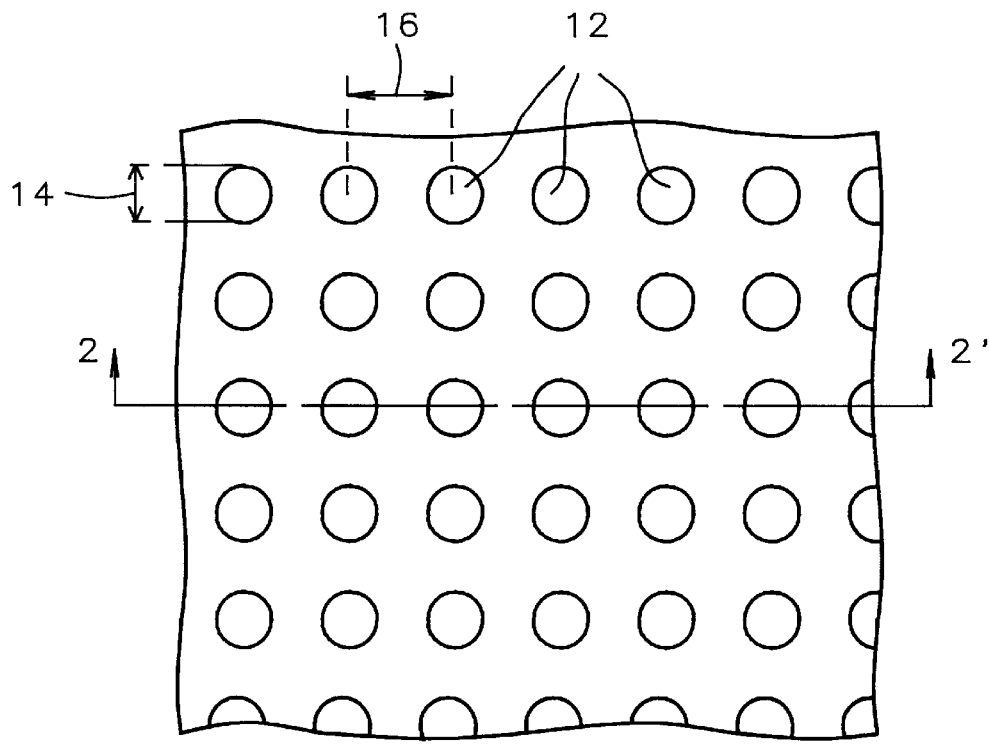
FIG. 1 shows a top view of a test pattern having an array of metal circles representing contact areas.
Figure 2:
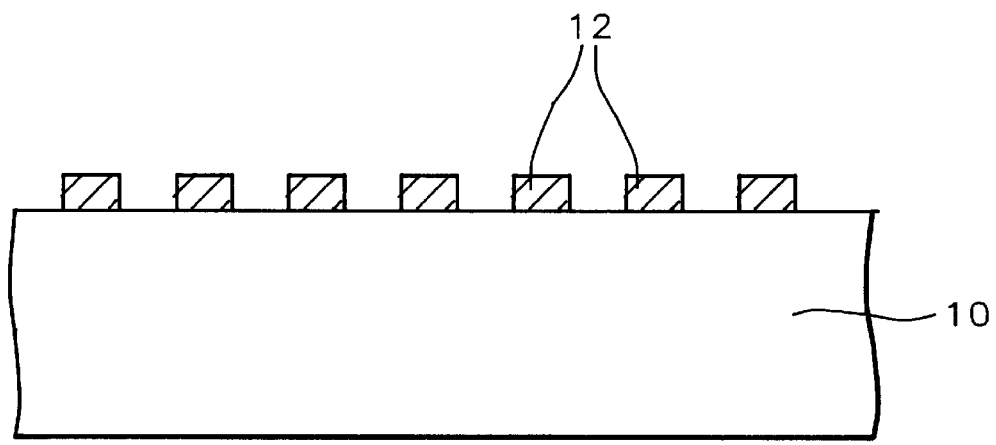
FIG. 2 shows a cross section view of a test pattern having an array of metal circles representing contact areas.

Refer now to FIGS. 1–6, there is shown an embodiment of test devices having metal test patterns to be used to monitor metal corrosion problems. FIGS. 1–6 shows top and cross section views of wafers having the metal test patterns of this invention used to determine the presence of metal corrosion problems. FIG. 1 shows a top view and FIG. 2 a cross section view of a test pattern having an array of metal circles 12 wherein each metal circle 12 has a diameter 14 of between about 0.3 and 2.0 micrometers formed on a substrate 10, such as a silicon wafer. The distance 16 between centers of adjacent metal circles is between about 0.3 and 2.0 micrometers. The metal circles are formed of metals such as aluminum, aluminum/silicon/copper, aluminum/copper, or the like and simulate contact regions on an integrated circuit wafer. The array of metal circles typically covers the entire wafer surface.

Figure 3:
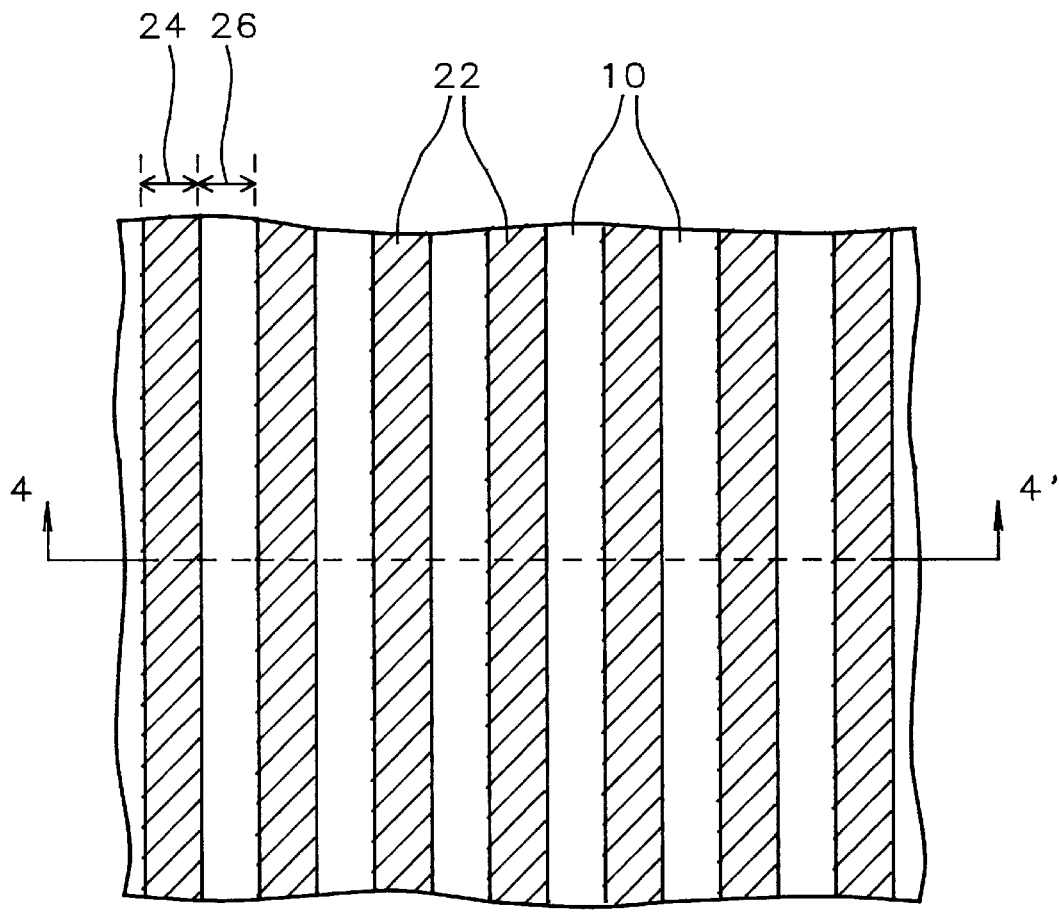
FIG. 3 shows a top view of a test pattern having an array of parallel metal strips representing electrodes.
Figure 4:
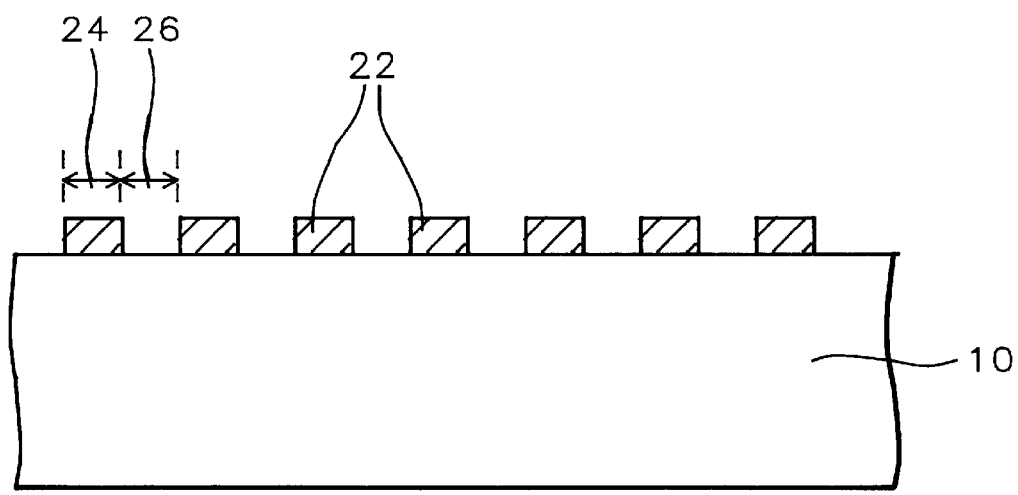
FIG. 4 shows a cross section view of a test pattern having an array of parallel metal strips representing electrodes.

FIG. 3 shows a top view and FIG. 4 a cross section view of a test pattern having an array of metal strips 22 wherein each strip has a width 24 of between about 0.5 and 2.0 micrometers formed on a substrate 10, such as a silicon wafer. The separation 26 between the nearest edges of adjacent metal strips is between about 0.5 and 2.0 micrometers. The metal strips are formed of metals such as aluminum, aluminum/silicon/copper, aluminum/copper, or the like and simulate metal electrode regions on an integrated circuit wafer. The array of metal strips typically covers the entire wafer surface. The metal strips 22 in FIG. 3 are cross hatched to aid the clarity of the drawing.

Figure 5:
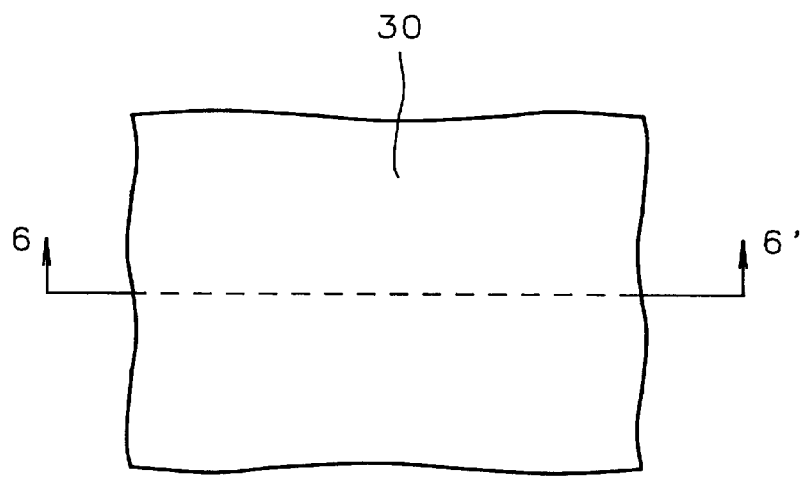
FIG. 5 shows a top view of a test pattern having a blanket metal layer.
Figure 6:
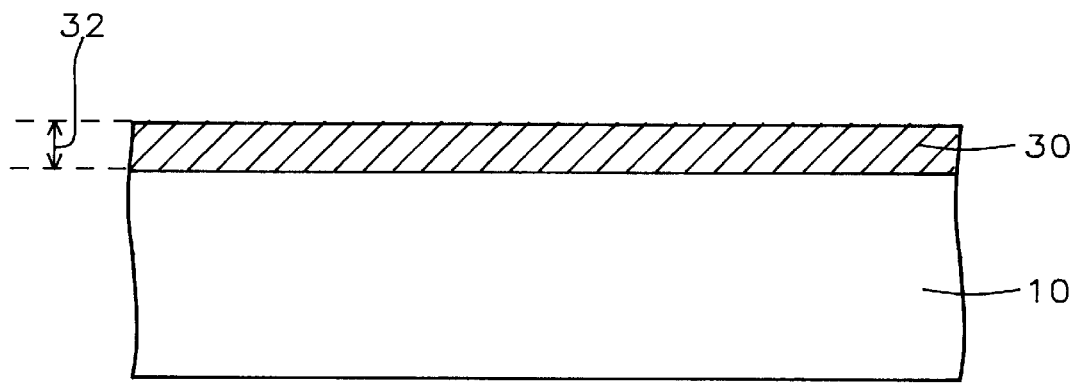
FIG. 6 shows a cross section view of a test pattern having a blanket metal layer.

FIG. 5 shows a top view and FIG. 6 a cross section view of a test pattern having a blanket metal layer 30 formed on a wafer 10. The metal layer 30 has a thickness 32 of between about 0.1 and 0.8 micrometers. The blanket metal layer 30 is formed of metals such as aluminum, aluminum/silicon/copper, aluminum/copper, or the like and simulates bulk metal regions on an integrated circuit wafer. The blanket metal layer typically covers the entire wafer surface.

The FIGS. 1–6 show the metal test patterns formed directly on the wafer surface, however those skilled in the art will readily recognize that a layer of dielectric or the like could be formed between the test patterns and the surface of the wafer. By measuring differences in the amounts of corrosion of the various test patterns it can readily be determined whether metal corrosion is more likely to affect contact regions, electrode regions, bulk metal regions, etc.

Refer now to FIGS. 1–7, there is shown an embodiment of a method for monitoring metal corrosion during the manufacture of integrated circuit wafers. FIGS. 1–6 shows top and cross section views of wafers having an array of metal circles, an array of metal strips, and a blanket metal layer as described previously. First the test devices or wafers having metal test patterns are formed using normal product processing steps and are processed along with normal product wafers. The metal test patterns are formed of aluminum, aluminum/silicon/copper, aluminum/copper, or the like.

Figure 7:
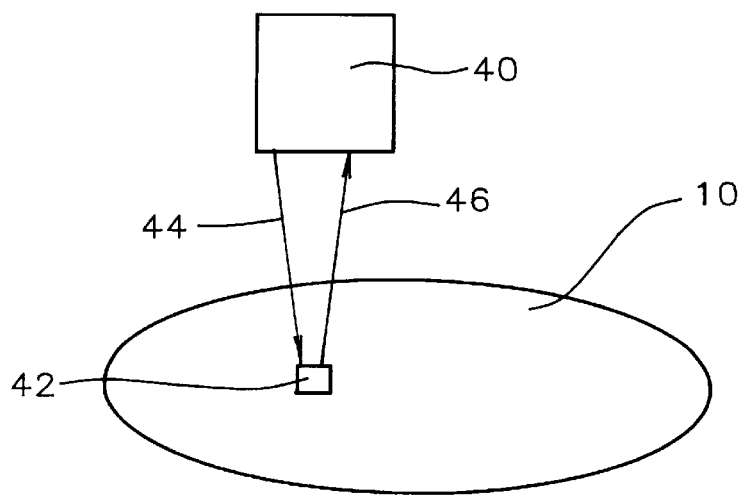
FIG. 7 shows a schematic diagram of a tool used to determine the number of defects per unit area of a test wafer.

Next, as shown in FIG. 7, a first number of test pattern defects per unit area for the wafers with the test patterns is measured using a defect detection tool 40. The defect detection tool 40, such as the LASER light-scattering and video image processing systems, are used to determine the number of defects per unit area for the test pattern being evaluated. The defect detection tool 40 has a means 42 for scanning a unit area 42 of the test wafer 10 with a light source and detecting optical information 46 from the test wafer 10 which can be related to the number of defects in that unit area 42. The scan is carried out over the wafer 10 surface and the number of defects per unit area is stored in the defect detection tool 40 or elsewhere.

Next, the test wafer is subjected to a stress environment, such as a relative humidity of between about 40% and 60% and a temperature of between about 20° C. and 30° C. for between about 2 and 6 hours. The stress environment will accelerate any potential corrosion of the metal test patterns. After the exposure to the stress environment is completed the wafers with the test patterns are returned to the defect detection tool 40 and a second number of defects per unit area is measured and stored either in the defect detection tool or elsewhere. A third number of defects per unit area is then determined as the difference between the second number of defects per unit area and the first number of defects per unit area for the same test pattern on the same wafer.

The third number of defects per unit area is then compared with a critical number of defects per unit area. The critical number of defects per unit area will depend on the actual test pattern being examined. If the third number of defects per unit area is less than the critical number of defects per unit area processing of the normal production wafers is continued. If the third number of defects per unit area is equal to or greater than the critical number of defects per unit area, this is an indication that there is a problem with the processing of normal production wafers. The defect per unit area results for the different type of test patterns can be used to determine the particular processing steps which need to be corrected. The process can be corrected before large numbers of defective production wafers are produced.

When the process defects have been corrected processing of new production wafers and test pattern wafers is begun.

While the invention has been particularly shown and described with reference to the preferred embodiments thereof, it will be understood by those skilled in the art that various changes in form and details may be made without departing from the spirit and scope of the invention.

What is claimed is:

1. A method for monitoring metal corrosion, comprising the steps of:

providing a wafer having a first surface and a metal test pattern formed on said first surface of said wafer;

providing means for determining the number of defects per unit area for said metal test pattern;

determining a first number of defects per unit area for said metal test pattern;

exposing said metal test pattern to a stress environment for a first time after determining said first number of defects per unit area, wherein said stress environment will accelerate any potential corrosion of said metal test pattern;

determining a second number of defects per unit area for said metal test pattern after exposing said metal test pattern to said environmental stress conditions;

determining a third number of defects per unit area wherein said third number of defects per unit area is the difference between said second number of defects per unit area and said first number of defects per unit area; and proceeding with wafer processing or stopping wafer processing depending on said third number of defects per unit area.

2. The method of claim 1 wherein said metal test pattern is formed of aluminum.

3. The method of claim 1 wherein said metal test pattern is formed of aluminum/silicon/copper.

4. The method of claim 1 wherein said metal test pattern is formed of aluminum/copper.

5. The method of claim 1 wherein said metal test pattern comprises a number of parallel metal strips having a width of between about 0.5 and 2.0 micrometers and a separation of between about 0.5 and 2.0 micrometers between the nearest edges of adjacent strips.

6. The method of claim 1 wherein said metal test pattern comprises an array of metal circles wherein each metal circle has a diameter of between about 0.3 and 2.0 micrometers and the distance between the centers of adjacent metal circles is between about 0.3 and 2.0 micrometers.

7. The method of claim 1 wherein said metal test pattern comprises a blanket metal layer having a thickness of between about 0.1 and 0.8 micrometers.

8. The method of claim 1 wherein said stress environment comprises relative humidity between about 40% and 60% and temperature between about 20° C. and 30° C.

9. The method of claim 1 wherein said first time is between about 2 and 6 hours.

10. The method of claim 1 wherein said metal test pattern covers the entire said first surface of said wafer.

* * * * *